US010328429B2

(12) United States Patent
Stein et al.

(10) Patent No.: US 10,328,429 B2
(45) Date of Patent: Jun. 25, 2019

(54) TEST ELEMENT ANALYSIS SYSTEM FOR THE ANALYTICAL EXAMINATION OF A SAMPLE

(71) Applicant: Roche Diagnostics Operations, Inc., Indianapolis, IN (US)

(72) Inventors: Reiner Stein, Bad Kreuznach (DE); Lars Fischheiter, Ludwigsburg (DE); Martin Mertens, Schriesheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 135 days.

(21) Appl. No.: 15/723,252

(22) Filed: Oct. 3, 2017

(65) Prior Publication Data
US 2018/0104683 A1    Apr. 19, 2018

(30) Foreign Application Priority Data

Oct. 14, 2016   (EP) .................................. 16193899

(51) Int. Cl.
*B01L 3/00* (2006.01)
*G01N 33/483* (2006.01)
(Continued)

(52) U.S. Cl.
CPC ................. *B01L 3/508* (2013.01); *B01L 9/00* (2013.01); *G01N 27/3273* (2013.01);
(Continued)

(58) Field of Classification Search
CPC .......... B01L 2200/025; B01L 2200/14; B01L 2300/0627; B01L 3/508; B01L 9/00;
(Continued)

(56) References Cited

U.S. PATENT DOCUMENTS 4,780,283 A    10/1988  Meinecke et al.
5,127,837 A *   7/1992  Shah .................... G01R 1/0408
                                                                439/248
(Continued)

FOREIGN PATENT DOCUMENTS

EP         0371003 B1    5/1990
EP         0376111 B1    7/1990
(Continued)

OTHER PUBLICATIONS

Hönes, Joachim et al., The Technology Behind Glucose Meters: Test Strips, Diabetes Technology & Therapeutics, 2008, pp. S-10-S-26, vol. 10, Supplement 1.

*Primary Examiner* — Jennifer Wecker
(74) *Attorney, Agent, or Firm* — Roche Diagnostics Operations, Inc.

(57) ABSTRACT

A test element analysis system for the analytical examination of a sample, a method for positioning a test element in a measuring device and a method for an analytical examination of a sample are disclosed. The test element analysis system comprises: a measurement device comprising a test element receptacle for receiving a test element at least partially, wherein the receptacle comprises a first part and a second part, the first part comprises a support surface for placement of the test element, the second part comprises an alignment pin for engagement with an alignment hole of the test element, the second part is movable relative to the first part in a direction essentially perpendicular to the support surface, the receptacle is configured to position the second part in at least three distinct positions relative to the first part comprising an intermediate position, a closed position, and an open position.

16 Claims, 4 Drawing Sheets

(51) Int. Cl.
    *B01L 9/00*          (2006.01)
    *G01N 27/327*      (2006.01)
    *G01N 27/416*      (2006.01)
    *G01N 33/487*      (2006.01)
    *G01N 21/78*       (2006.01)

(52) U.S. Cl.
    CPC ..... *B01L 2200/025* (2013.01); *B01L 2200/14* (2013.01); *B01L 2300/0627* (2013.01); *G01N 21/78* (2013.01); *G01N 27/416* (2013.01); *G01N 33/4875* (2013.01)

(58) Field of Classification Search
    CPC .. G01N 21/78; G01N 27/3273; G01N 27/416; G01N 33/4875
    See application file for complete search history.

(56) References Cited

U.S. PATENT DOCUMENTS

| | | |
|---|---|---|
| 7,041,254 B2 | 5/2006 | Haviland et al. |
| 2015/0177174 A1 | 6/2015 | Elder et al. |

FOREIGN PATENT DOCUMENTS

| | | | | |
|---|---|---|---|---|
| EP | 1271150 A2 * | 1/2003 | ........... | G01N 33/558 |
| EP | 1271150 A2 | 1/2003 | | |

\* cited by examiner

TEST ELEMENT ANALYSIS SYSTEM FOR THE ANALYTICAL EXAMINATION OF A SAMPLE

CROSS-REFERENCE TO RELATED APPLICATIONS

This application claims priority to European Patent Application No. 16193899.8, filed 14 Oct. 2016, the disclosure of which is hereby incorporated by reference in its entirety.

FIELD OF THE DISCLOSURE

The present disclosure relates to a test element analysis system for the analytical examination of a sample, a method for positioning a test element in a measuring device for performing an analytical examination of a sample, in particular a body fluid, and a method for an analytical examination of a sample, in particular a body fluid. The devices and methods according to the present disclosure mainly may be used in the field of qualitatively or quantitatively detecting at least one analyte in a sample, such as a sample of a body fluid, and/or for determining at least one parameter of the sample. Other fields of application are feasible.

BACKGROUND

In the field of medical technology and diagnostics, a large number of devices and methods for determining the presence and/or the concentration of one or more analytes in samples, specifically fluid samples, such as body fluids, and/or for determining at least one parameter of a sample are known. Without restricting the scope of the present disclosure, in the following, mainly reference is made to the determination of coagulation parameters or analyte concentrations in blood samples, e.g., to the determination of blood glucose or ketone body concentrations. As an example, reference may be made to commercially available devices and systems, such as the ACCU-CHEK® INFORM systems, the COAGUCHEK® systems or the REFLOTRON® systems, all by Roche Diagnostics GmbH, Germany. It shall be noted, however, that other types of samples or other types of analytes or parameters may be used in a similar way.

For performing fast and simple measurements, several types of test elements are known, which mainly are based on the use of one or more test chemicals, i.e., on the use of one or more chemical substances, one or more chemical compounds or one or more chemical mixtures, adapted for performing a detection reaction for detecting the analyte or determining the parameter. The test chemical often is also referred to as a test substance, a test reagent, a test chemistry or as a detector substance. For details of potential test chemicals and test elements comprising such test chemicals, which may also be used within the present disclosure, reference may be made to J. Hoenes et al.: The Technology Behind Glucose Meters: Test Strips, Diabetes Technology & Therapeutics, Vol. 10, Supplement 1, 2008, S-10 to S-26. Other types of test elements and/or test substances are feasible and may be used within the present disclosure.

By using one or more test chemicals, a detection reaction may be initiated, the course of which depends on the presence and/or the concentration of the at least one analyte or on the parameter to be determined. The detection reaction preferably may be analyte-specific. Typically, as may also be the case in the present disclosure, the test chemical is adapted to perform at least one detection reaction when the analyte is present in the body fluid, wherein the extent and/or the degree of the detection reaction typically depends on the concentration of the analyte. Generally, the test chemical may be adapted to perform a detection reaction in the presence of the analyte, wherein at least one detectable property of at least one of the body fluid and the test chemical is changed due to the detection reaction. The at least one detectable property generally may be selected from a physical property and a chemical property. In the following, without restricting potential other embodiments, reference will mainly be made to detection reactions in which one or more physical properties are changed due to the detection reaction, such as one or more of at least one electrical property and at least one optical property. Further, without restricting alternative solutions, reference will be made to detection reactions in which at least one chemical property which is optically detectable is changed, i.e., to optical test elements. Other test elements, such as combined optical and electrical test elements, however, are usable, too.

One technical challenge in typical analyte measurement systems using a measurement device and a test element, also referred to as a test carrier, resides in an accurate and precise positioning of the test element, in particular of the test field of the test element. Specifically in optical measurement systems, and also in many electrochemical measurement systems or measurement systems using both optical and electrochemical measurements, the test field has to be aligned precisely within a measurement device. Thus, as an example, in optical measurement systems, an optical area of the test element, such as an optical test field, and the optical detection system of the analytical device, which is also often referred to as a meter, have to be aligned. For this purpose, several technologies are known, such as the use of alignment pins or the use of electrical connectors of the measurement device for positioning purposes. Still, specifically in case electrical connectors are used for positioning, the precision of alignment remains to be an issue.

Despite the advantages achieved by the above-mentioned prior art technologies, several technical challenges remain. Thus, as an example, test elements are known which make use of both optical and electrochemical measurement principles. In case both of these detection methods are used, the test carrier typically has to be aligned precisely with respect to the optical detection system and, further, has to be electrically coupled to an electrical connector. Simultaneously achieving and fulfilling these requirements and targets, however, often imposes some severe design constraints. In many cases, electrical connectors having desired tolerances are not available. The fixation of the test element at two different positions, such as by using an alignment pin and an electrical connector, causes and over determination of the fixation which, often, suffers from insufficient tolerances of the alignment elements.

Further, in some systems, a closing of the test element receptacle and fixation of the test element within the test element receptacle is initiated by the test element itself, acting on a lever or the like. In these systems, the test element may be bent due to forces acting on the test element in a longitudinal direction which may lead to a misalignment of the test element. In other systems, separating the insertion of the test element and the clamping or fixation of the test element, a time delay may occur in between the insertion and the fixation, during which a misalignment may occur. Specifically in case a user is moving with a handheld system, there is a high risk for mechanical shocks or movements in between the insertion of the test strip and the closing of the measurement device. In this case, the test element, now being misaligned, may even be destroyed by the subsequent closing of the test element receptacle of the measurement device.

A further challenge resides in the fact that the test element, during use, has to be secured against external forces. Thus, as an example, a user may try to pull out a test strip during measurement or in other situations in which the test strip is fixed within the measurement device.

SUMMARY

It is against the above background that the present disclosure provides certain unobvious advantages and advancements over the prior art. In particular, the inventors have recognized a need for improvements in test element analysis systems for the analytical examination of a sample.

Although the embodiments of the present disclosure are not limited to specific advantages or functionality, it is noted that the present disclosure provides a test element analysis system, a method for positioning a test element in a measuring device for performing an analytical examination of a sample and a method for an analytical examination of a sample that allow for a precise and reliable positioning of the test element, thereby increasing mechanical stability and reproducibility of measurements.

In accordance with one embodiment of the present disclosure, a test element analysis system for the analytical examination of a sample is provided, comprising a measurement device, the measurement device comprising a test element receptacle for receiving at least one test element at least partially, wherein the test element receptacle comprises at least one first part and at least one second part, wherein the first part comprises at least one support surface for placement of the test element, wherein the second part comprises at least one alignment pin for engagement with at least one alignment hole of the test element, wherein the second part is movable relative to the first part in a direction essentially perpendicular to the support surface, wherein the test element receptacle is configured to position the second part in at least three distinct positions relative to the first part, the at least three distinct positions comprising an intermediate position for inserting the test element into the test element receptacle, a closed position for performing a measurement and an open position for removing the test element from the test element receptacle, wherein in the closed position the alignment pin protrudes through the alignment hole, wherein in the open position the first part and the second part are spaced apart such that the test element may freely be removed from the test element receptacle, and wherein in the intermediate position the first part and the second part are spaced apart such that the test element may be inserted into the test element receptacle, whereas the alignment pin is positioned such that the test element is resiliently deformed by the alignment pin during the insertion, until the alignment pin snaps into the alignment hole.

In accordance with another embodiment of the present disclosure, a method for positioning a test element in a measuring device for performing an analytical examination of a sample is provided, the method comprising: a) providing a measurement device having a test element receptacle for receiving at least one test element at least partially, wherein the test element receptacle comprises at least one first part and at least one second part, wherein the first part comprises at least one support surface for placement of the test element, wherein the second part comprises at least one alignment pin for engagement with at least one alignment hole of the test element, wherein the second part is movable relative to the first part in a direction essentially perpendicular to the support surface, b) positioning the second part in an intermediate position, wherein in the intermediate position the first part and the second part are spaced apart such that the test element may freely be inserted into the test element receptacle, c) inserting at least one test element having at least one alignment hole into the test element receptacle, wherein the test element is temporarily and resiliently deformed by the alignment pin during the insertion, until the alignment pin snaps into the alignment hole, d) positioning the second part in a closed position, wherein in the closed position the alignment pin protrudes through the alignment hole, e) positioning the second part in an open position, wherein in the open position the first part and the second part are spaced apart, and f) removing the test element from the test element receptacle.

In accordance with yet another embodiment of the present disclosure, a method for an analytical examination of a sample is provided, wherein the method comprises the method steps according to the embodiment recited directly above, and wherein the method further comprises at least one measurement step for detecting at least one analyte in the sample.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
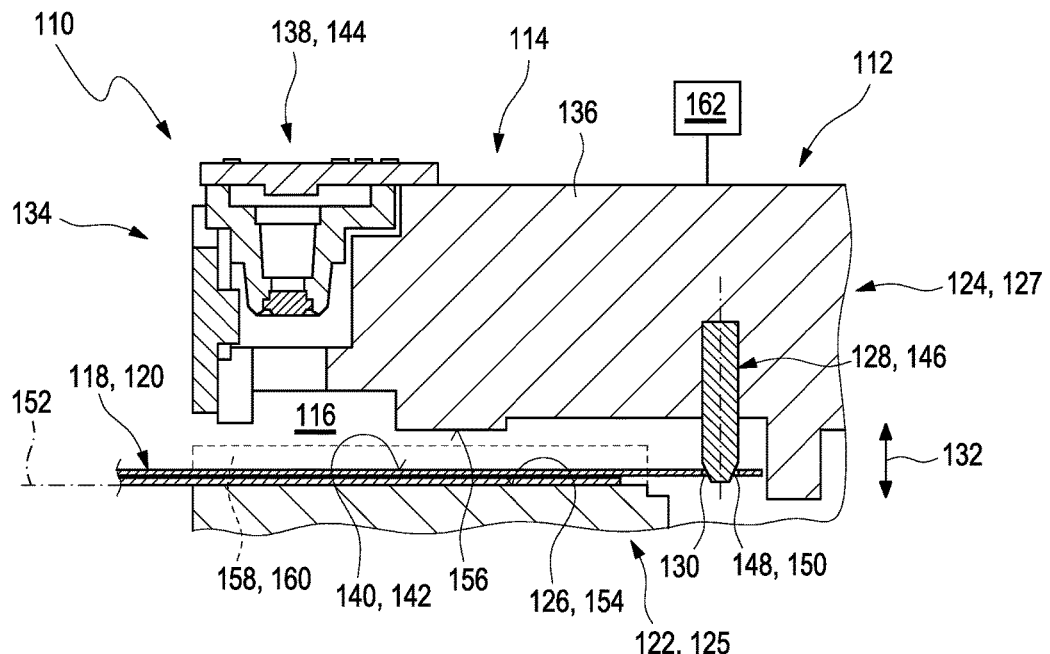
FIG. 1A shows details of a test element analysis system in accordance with an embodiment of the present disclosure in a cross-sectional view.
FIG. 1B shows a detailed view of a part of the test element analysis system in accordance with an embodiment of the present disclosure in a cross-sectional view.
Figure 1:
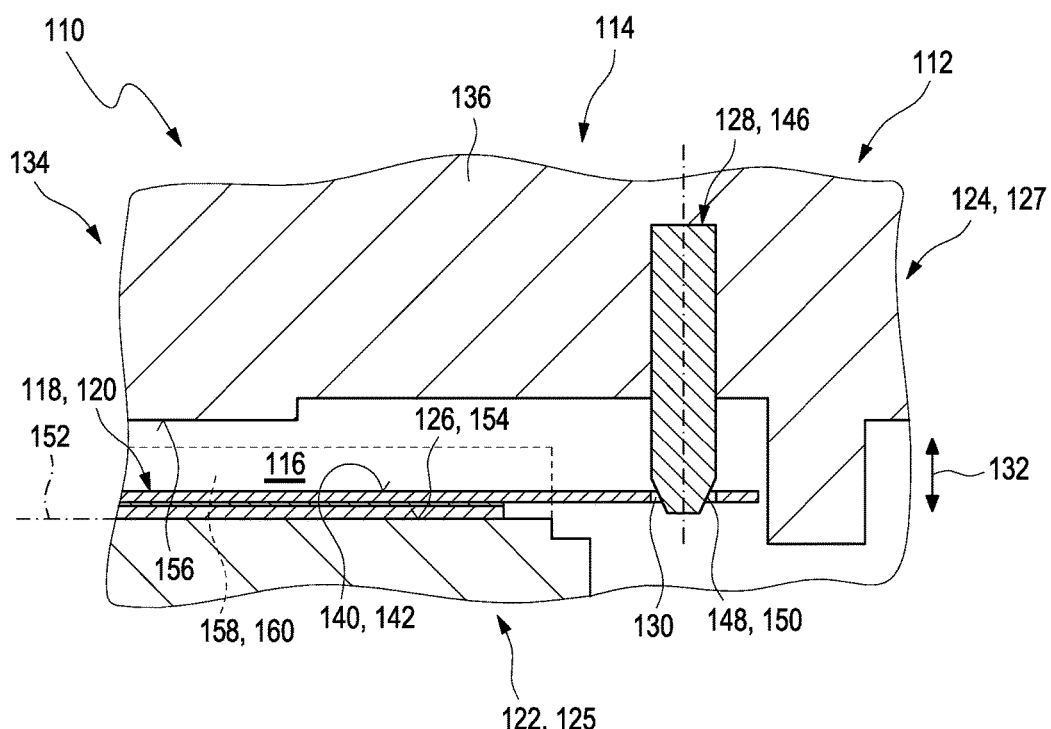
Figure 2:
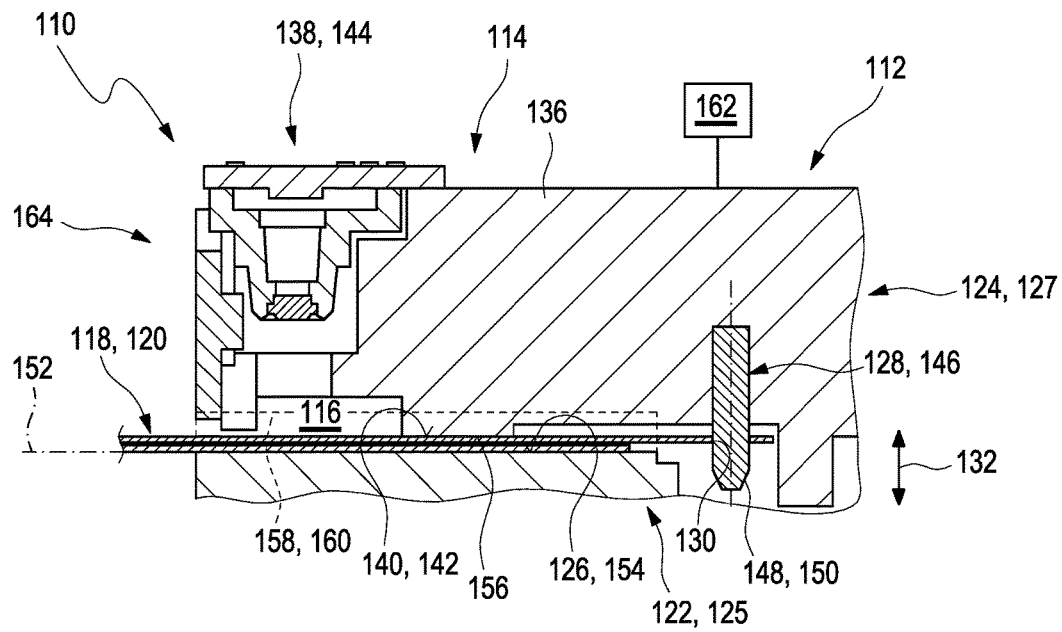
FIG. 2A shows details of a test element analysis system in accordance with an embodiment of the present disclosure in a cross-sectional view.
FIG. 2B shows a detailed view of a part of the test element analysis system in accordance with an embodiment of the present disclosure in a cross-sectional view.
Figure 2:
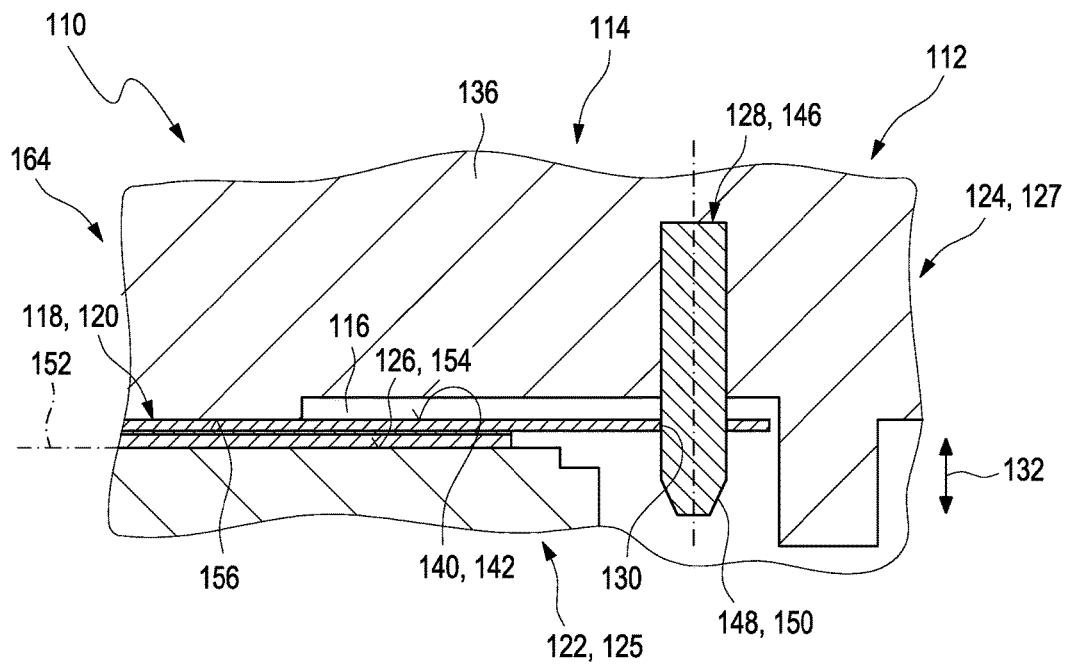
Figure 3:
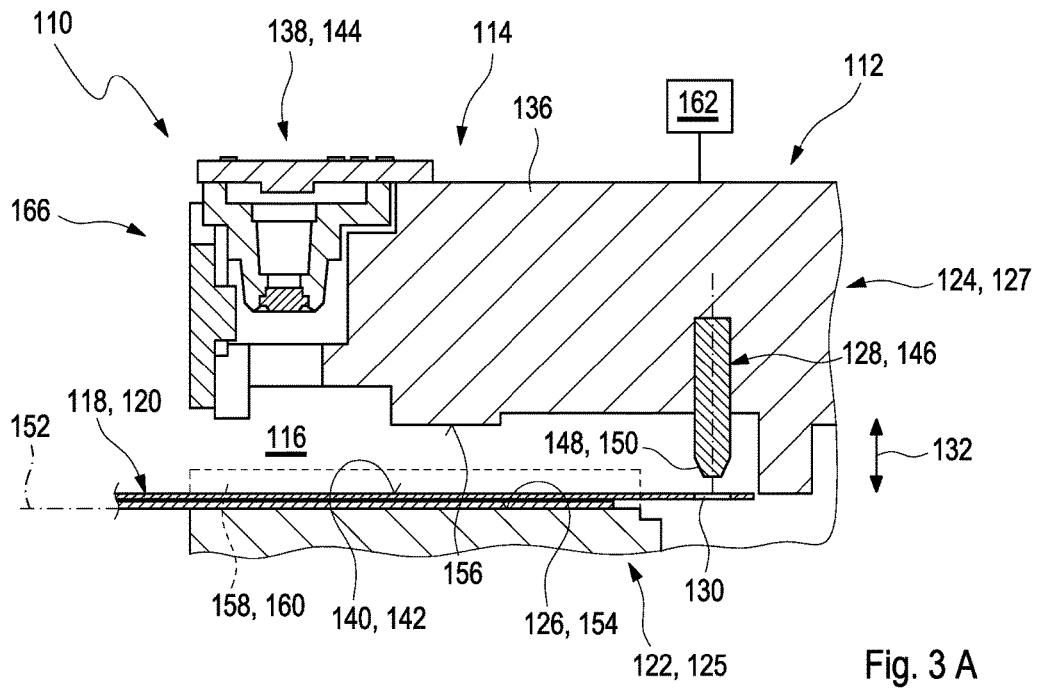
FIG. 3A shows details of a test element analysis system in accordance with an embodiment of the present disclosure in a cross-sectional view.
FIG. 3B shows a detailed view of a part of the test element analysis system in accordance with an embodiment of the present disclosure in a cross-sectional view.
Figure 3:
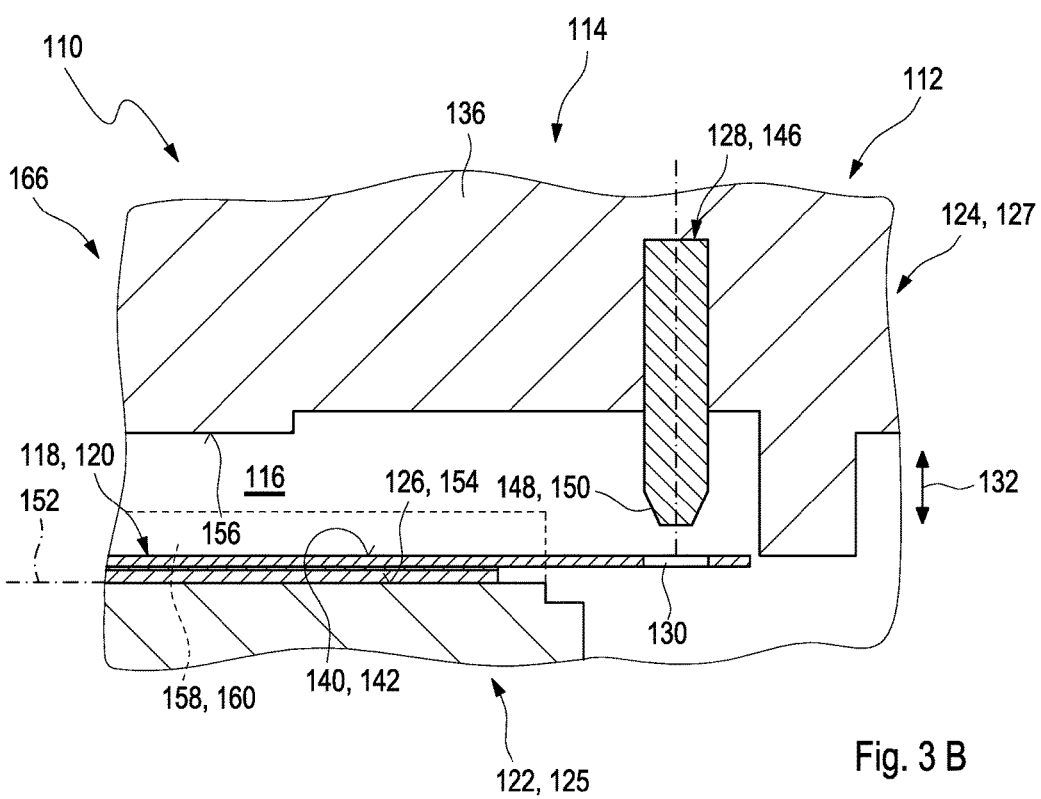

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

As generally used within the present disclosure, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the disclosure may be applied to other types of users or patients or diseases.

In accordance with an embodiment of the present disclosure, a test element analysis system for the analytical examination of a sample, in particular of a body fluid, is disclosed. The test element analysis system comprises a measurement device. The measurement device comprises a test element receptacle for receiving at least one test element, specifically a test strip, at least partially. The test element receptacle comprises at least one first part and at least one second part. The first part comprises at least one support surface for placement of the test element and the second part comprises at least one alignment pin for engagement with at least one alignment hole of the test element. The second part is movable relative to the first part in a direction essentially perpendicular to the support surface. The test element receptacle is configured to position the second part in at least three distinct positions relative to the first part. The at least three distinct positions comprise an intermediate position for inserting the test element into the test element receptacle, a closed position for performing a measurement and an open position for removing the test element from the test element receptacle. In the closed position the alignment pin protrudes through the alignment hole. In the open position the first part and the second part are spaced apart such that the test element may freely be removed from the test element receptacle. Further, in the intermediate position the first part and the second part are spaced apart such that the test element may be inserted into the test element receptacle, whereas the alignment pin is positioned such that the test element is resiliently deformed by the alignment pin during the insertion, until the alignment pin snaps into the alignment hole As further used herein, the term "being resiliently deformed" refers to an arbitrary property of an element of being temporarily deformable in a manner such that the element is able to return to an original shape after being pulled, stretched, pressed, bent, etc., such as after a being deformed in general.

As further used herein, the term "system" refers to an arbitrary set of interacting or interdependent component parts forming a whole. Specifically, the components may interact with each other in order to fulfill at least one common function. The at least two components may be handled independently or may be coupled or connectable. Thus, the term "test element analysis system" generally refers to a group of at least two elements or components that are capable of interacting in order to perform at least one analytical detection, specifically at least one analytical detection of at least one analyte of the sample, by interacting with an arbitrary test element. The test element analysis system may generally also be referred to as an analytical system, an analytical kit, a sensor system or a measurement system.

As further used herein the term "sample" may refer to an arbitrary material or combination of materials taken for an analysis, testing or investigation. The sample may be a limited quantity of something that is intended to be similar to and represent a larger amount. However, the sample may also comprise a full specimen. The sample may be solid sample, a liquid sample or a gaseous sample or a combination of these. Specifically, the sample may be a fluid sample, i.e., a sample which fully or partially is in a liquid state and/or in a gaseous state. A quantity of the sample may be describable in terms of its volume, mass or size. However, other dimensions are feasible. The sample may comprise only one material or only one compound. Alternatively, the sample may comprise several materials or compounds.

The term "analyte" generally refers to an arbitrary element, component or compound that may be present in the sample and the presence and/or the concentration of which may be of interest for the user, the patient or medical staff such as a medical doctor. Particularly, the analyte may be or may comprise an arbitrary chemical substance or chemical compound that may take part in the metabolism of the user or the patient, such as at least one metabolite. The detection of the at least one analyte specifically may be an analyte-specific detection.

As further used herein, the term "body fluid" may refer to a fluid that typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids. During detection of the at least one analyte, the body fluid may be present within the body or body tissue. Thus, specifically, as will be outlined in further detail below, the sensor may be configured for detecting at least one analyte in a body tissue.

The term "analytical examination" generally may refer to a process of determining the presence and/or the quantity and/or the concentration of the at least one analyte or to a process of determining a parameter of the sample that is characteristic of the properties of the sample, e.g., glucose. The analytical examination may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced that characterizes an outcome of the detection, such as at least one measurement signal. The at least one measurement signal specifically may be or may comprise at least one electronic signal such as at least one voltage and/or at least one current. The at least one signal may be or may comprise at least one analogue signal and/or may be or may comprise at least one digital signal.

As described above, the measurement device comprises the test element receptacle for receiving the at least one test element at least partially. Specifically, the test element analysis system may comprise at least one test element having at least one alignment hole. The term "test element" may generally refer to an arbitrary device that is capable of detecting the analyte in the sample or of determining the parameter of the sample. The test element may specifically be a strip-shaped test element. As used herein, the term "strip-shaped" refers to an element having an elongated shape and a thickness, wherein an extension of the element in a lateral dimension exceeds the thickness of the element, such as by at least a factor of 2, typically by at least a factor of 5, more typically by at least a factor of 10 and most typically by at least a factor of 20 or even at least a factor of 30. Thus, the test element may also be referred to as test strip.

The test element may have at least one test field comprising at least one test chemical for performing at least one detection reaction in the presence of an analyte contained in the sample, specifically glucose. The term "test chemical", also referred to as a test chemistry, may refer to an arbitrary material or a composition of materials adapted to change at least one detectable property in the presence of the analyte. Generally, this property may be selected from an electrochemically detectable property and/or an optically detectable property, such as a color change and/or a change in remissive properties. Specifically, the test chemistry may be a highly selective test chemistry, which only changes the property if the analyte is present in the sample of the body fluid applied to the test element, whereas no change occurs if the analyte is not present. More typically, the degree or change of the property may be dependent on the concentration of the analyte in the body fluid, in order to allow for a quantitative detection of the analyte.

The test chemical may be configured for performing at least one of an electrochemical detection reaction and an optical detection reaction. The electrochemical detection reaction and/or the optical detection reaction may be analyte specific. Further, the electrochemical detection reaction and/or the optical detection reaction may be a qualitative and/or a quantitative detection. As used herein, the term "optical detection reaction" refers to a detection of an optical detectable property of the analyte itself or an auxiliary compound that is produced or converted within a detection reaction depending on the presence and/or concentration of the analyte in the sample, such as a color change and/or a change in remissive properties.

As used herein, the term "electrochemical detection reaction" refers to a detection of an electrochemically detectable reaction of the analyte by electrochemical means. Further, the term "electrochemically detection" may refer to a detection of an electrochemically detectable property of at least one arbitrary analyte, such as an electrochemical detection reaction. Thus, for example, the electrochemical detection reaction may be detected by comparing one or more electrode potentials, such as an electrostatic potential of a working electrode with the electrostatic potential of one or more further electrodes such as a counter electrode or a reference electrode. Thus, the test element may exemplarily be an electrochemical test element. The term "electrochemical test element" may refer to an arbitrary test element configured for conducting at least one electrochemical detection.

As described above, the test element may have the at least one test field comprising the at least one test chemical for performing at least one detection reaction in the presence of an analyte contained in the sample. As further used herein, the term "test field" may refer to an arbitrary area or region of an object wherein an arbitrary measurement, specifically an analytical measurement, is conducted. Specifically, the test field may be capable of performing at least one change being characteristic for an analyte or a parameter. The test chemical as described above may be located within the test field, particularly on at least one surface of the test field. Thus, the test field may also be referred to as measuring zone or measuring field.

Further, the test element may comprise at least one capillary configured for receiving and transporting the sample. The term "capillary" generally refers to an arbitrary elongate void volume or lumen such as a small tube or slot, which is capable exerting capillary actions onto a liquid or fluid. Generally, the capillary may comprise dimensions in the millimeter or sub-millimeter range. Commonly, a fluidic medium may migrate through the capillary by capillary action wherein the fluidic medium may flow in narrow spaces of the capillary without an assistance of external forces like gravity due to intermolecular forces between the fluidic medium and a surface of the capillary facing the fluidic medium.

As described above, the test element analysis system comprises the measurement device. As further used herein, the term "measurement device" may refer to an arbitrary device, typically an electronic device, which is configured to detect at least one signal. The signal may be an optical signal and/or an electrochemical signal. The measuring device may be handled independently from the test element and may be adapted to interact with the test element in order to perform an analysis, such as by detecting the at least one signal. Thus, the term "measurement device" may often also be referred to as a measuring device, as an analytical device, as a meter or as a test device.

The measurement device may further comprise at least one evaluation device for evaluating at least one measurement performed with the measurement device, specifically at least one processor. As used herein, the term "evaluation device" may refer to an arbitrary device being configured to derive at least one item of information from data. Specifically the evaluation device may be configured to derive the at least one item of information regarding the presence and/or concentration of the analyte in the body fluid or a parameter of the body fluid from at least one signal.

The measurement device may comprise at least one detector for detecting at least one detection reaction between the sample or at least one component thereof and at least one constituent of the test element, specifically at least one test chemical of the test element. Specifically, the detector may be fully or partially comprised in the second part. Exemplarily, the detector may be part of the second part or may be formed as a component of the second part. Thus, the detector may be configured to be moved when the second part is moved. However, other embodiments may be feasible. The alignment pin may be configured to position the test element relative to the detector. As used herein, the term "detector" may refer to an arbitrary device that is configured to detect events or changes in its environment and to provide a corresponding output or signal. The detector may exemplarily be an optical detector. The term "optical detector" may generally refer to an arbitrary optical instrument configured for receiving electromagnetic radiation, typically light in the infrared and/or visible and/or ultraviolet spectral range. Thus, the optical detector may be configured for recording images, which may be stored locally, transmitted to another location or both. Further, the detector may exemplary be an electrochemical detector. The term "electrochemical detector" may generally refer to an arbitrary electrochemical instrument configured for determining an electric current or potential generated by an electrochemical reaction.

As described above, the measurement device comprises the test element receptacle for receiving the at least one test element at least partially, i.e., fully or partially. As further used herein, the term "receptacle" may generally refer to a free volume of an arbitrary element that is configured to at least partially receive or hold another object. Thus, the receptacle may have a shape that at least widely corresponds to the other object or vice versa. Exemplarily, the other object, or at least an insertable portion of the other object may have a rectangular shape and the receptacle may have a rectangular shape as well. The term "test element receptacle" generally may refer to an arbitrary receptacle that is configured to receive or to hold an arbitrary test element. The test element receptacle may have an elongated shape extending along a longitudinal axis. Thus, the test element receptacle may provide an elongated channel, slot or opening having a cross-section that corresponds to the cross-section of the test element and into which the test element may be inserted. Other embodiments may be feasible. The test element may specifically be configured to be put reversibly into the test element receptacle. Specifically, the test element may be configured to be positioned on a specific position within the test element receptacle such that a movement of the test element in at least one direction may be suppressed at least to a large extent. Thus, the test field of the test element may be located in a predetermined position relative to the measurement device. Further, inside the test strip receptacle, one or more port interfaces may be provided for electrically and/or optically interacting with the test strip. The interfaces may exemplarily be or may comprise one or more ports. Additionally or alternatively, other kinds of interfaces may be feasible.

The test element may at least partially be received in the test element receptacle. The term "receiving" may generally refer to a condition of an object of being located or inserted fully or at least partially into a receptacle or into an opening of another element. Thus, a part of the object may be located outside of the other element. Alternatively, the test element may fully be located or accommodated in the test element receptacle.

The test element receptacle may be shaped complementary to the test element. Therefore, the test element receptacle and the test element may be configured to establish a form-fit connection.

Specifically, the test element receptacle may be configured to hold the test strip in the predetermined position, such as by using the alignment pin. Further, other holding elements such as spring elements may be applied. Beyond, the test strip receptacle may be configured to form a counter-bearing. The counter-bearing may be configured to be pressed against the test element.

The test element receptacle may further comprise a lateral guiding for the test element. As further used herein, the term "lateral guiding" may refer to an arbitrary element that is configured to support a movement of another object within a desired direction, specifically within a desired lateral direction. Therefore, the lateral guiding may specifically prevent at least to a large extent a rotation of the test element within the test element receptacle when the alignment hole is engaged by the alignment pin. Specifically, a rotation of the test element around the alignment pin and/or an axis defined by the alignment pin may be prevented at least to a large extent. Specifically, the lateral guiding may comprise a sidewall of the test element receptacle. Further, the test element receptacle may comprise at least one guiding element for guiding a relative movement of the second part and the first part. The guiding element may be part of the lateral guiding or vice versa. As further used herein, the term "guiding element" may refer to an arbitrary element that is configured to support a movement of another object within a desired direction. Specifically, the guiding element may comprise at least one guide rail, more typically at least one linear guide rail. Further, the test element receptacle may comprise at least one abutment element. The abutment element, in the intermediate position, may be configured for limiting an insertion of the test element into the test element receptacle. Specifically, the abutment element may be movable in a direction of insertion of the test element and the abutment element may be configured for ejecting the test element after use, when the test element receptacle is in the open position.

As described above, the test element receptacle comprises at least one first part and at least one second part. As further used herein, the term "part" refers to an arbitrary component of an object. Thus, several components interact with each other and may form a whole. The components of the object may be handled independently or may be coupled or connectable to each other. The terms "first part" and "second part" may be considered as nomenclature only, without numbering or ranking the named elements, without specifying an order and without excluding a possibility that several kinds of first parts and second parts may be present. Further, additional parts such as one or more third parts may be present.

As described above, the first part comprises the support surface for placement of the test element. As further used herein, the term "support surface" refers to an arbitrary surface that is configured to hold an arbitrary element. Specifically, the support surface may be configured to establish a close connection to the element. Therefore, the element may be configured to lie slackly on the support surface. Thus, the support surface may be an essentially flat surface.

As described above, the second part comprises the alignment pin for engagement with the alignment hole. As further used herein, the term "pin" may refer to an arbitrary element that is configured for fastening another object. Therefore, the pin may specifically have an elongate shape and may further have a tip that is configured to rest on a surface. The term "alignment pin" may generally refer to an arbitrary pin that is configured to arrange another object in a desired position and to prevent at least to a large extent a movement of the object in at least one position. The alignment pin may specifically be or may comprise a cylindrical alignment pin, typically a cylindrical alignment pin having a circular cross-section. Further, the alignment pin may have at least one tip, specifically at least one tapered tip. As further used herein, the term "tapered tip" may specifically refer to a tip wherein an end of the tip has a cross-section that is smaller than a cross-section within a central section of the pin. The tapered tip may exemplarily have a shape selected from the group consisting of a conical shape, a round shape, a tapered tip with a one-sided flat slope. Specifically, the alignment pin may have a cylindrical portion and a tapered tip, wherein, in the closed position, the cylindrical portion may be inside the alignment hole, wherein, in the intermediate position, after the alignment pin has snapped into the alignment hole, the tapered tip may be inside the alignment hole. Specifically, the tip, in the intermediate position, may penetrate a plane through the support surface, wherein, in the open position, the alignment pin may not penetrate the plane through the support surface. Further, in the closed position, the alignment pin, specifically the tapered tip of the alignment pin, may penetrate the plane through the support surface.

As further used herein, the term "alignment hole" may refer to an arbitrary hole within an element that is configured for an arrangement of the element within a desired position. Thereby, a movement of the element may be prevented at least to a large extent in at least one direction. The alignment hole may be specifically configured to be penetrated by an object that is configured to fix hold the element within at least one position. Specifically, the alignment hole may have a shape and a cross-section that correspond to the alignment pin, respectively.

Further, the second part may comprise at least one abutment surface interacting with the support surface or with a test element located on this support surface in the closed position. Thereby, in the closed position, the abutment surface may rest on the test element. The term "resting" may refer to a property of an element of staying on or within another object. Thereby, a movement of element relative to the object may be prevented at least to a large extent. As further used herein, the term "abutment surface" may refer to a surface of an arbitrary element that is configured to hold or to support an object, which is positioned onto the surface. Thereby, the abutment surface may specifically be or may comprise a flat, elongate surface providing a contact surface for the test element. Further, a movement of the test element may be prevented at least to a large extent in at least one direction. The abutment surface may be essentially parallel to the support surface. Thereby, the term "essentially parallel" may refer to a property of the abutment surface of being parallel to the support surface. Exemplarily, the abutment surface may be exactly parallel to the support surface. However, small deviations may be feasible. Specifically, the abutment surface may be arranged at an angle of +/− 20°, typically of +/−10°, more typically of +/−5° to the support surface. Further, the alignment pin may protrude from the abutment surface. Thereby, the term "protruding" may refer a property of an arbitrary element of sticking out from another object. Specifically, the alignment pin may be located essentially perpendicular to the abutment surface. As further used herein, the term "essentially perpendicular" may refer to a property of two or more objects being arranged exactly perpendicular to each other or with slight deviations. Specifically, the alignment pin may be positioned at an angle of 90° +/− 20°, typically of 90° +/−10°, more typically of 90° +/−5°, to the abutment surface.

As described above, the second part is movable relative to the first part in a direction essentially perpendicular to the support surface. Exemplarily, the first part may rest while the second part moves. Alternatively, the first part may move and the second part rests. Moreover, the first part and the second part may move, respectively. Thereby, the term "essentially perpendicular" may refer to a state wherein the first part and the second part are positioned exactly perpendicular to each other or with a slight deviation from the exact perpendicular position. Exemplarily, the first part and the second part may be positioned at an angle of 90° +/−30° relative to each other, typically at an angle of 90° +/−20°, more typically of 90° +/−10°, most typically of 90° +/−5°.

Specifically, the first part may form a fixed subassembly and the second part may form a moveable subassembly of the test element receptacle. As further used herein, the term "subassembly" may refer to a component or a group of components that form part of a whole assembly, specifically of a device. Further, the term "moveable subassembly" may refer to a subassembly that is moveable in at least one direction, specifically relative to another subassembly. On the contrary, the term "fixed subassembly" may refer to a subassembly that may stay or rest in a position, specifically in a desired position, such that a movement of the subassembly may be prevented at least to a large extent. Specifically, the second part may be moveable in a linear fashion relative to the first part.

The second part may comprise a block that is linearly moveable in a direction essentially perpendicular to the support surface. The term "block" may generally refer to an arbitrary element that may be made of a solid material. Specifically, the block may have a rectangular or a cubic shape. Still, other embodiments are feasible. The block may comprise at least one flat surface, e.g., a flat abutment surface. Thereby, the alignment pin may be at least partially and/or integrated into the block. The terms "moveable in a linear fashion" and "linearly moveable" may refer to a property of an arbitrary element of being capable of being moved in a straight manner such as on a virtual straight line. Thereby, the virtual straight line may be at least essentially free from bends. Further, the terms "moveable in a linear fashion" and "linearly moveable" may refer to a property of an arbitrary element of being capable of being moved in a constant way, such as, with a constant velocity.

Generally, the term "position" may generally refer to a spatial location of an object. Further, the term "positioning" may refer to an arbitrary process of bringing an object into a desired position such as by moving the object into the desired position. The terms "closed position", "intermediate position" and "open position" may be considered as nomenclature only, without numbering or ranking the named elements, without specifying an order and without excluding a possibility that several kinds of closed positions, intermediate positions and open positions may be present. Further, additional positions may be present.

The test element may be configured to be inserted into the receptacle. Thereby, the term "inserting" may refer to a process of placing an arbitrary element at least partially into another object such as into a receptacle of the object. The test element analysis system may be configured such that the test element may be inserted into the test element receptacle when the second part is in the intermediate position. Thus, the term "intermediate position" may refer to a position wherein the first part and the second part are spaced apart such that the test element may be inserted into the test element receptacle. As described above, the alignment pin is positioned such that the test element is temporarily and resiliently deformed by the alignment pin during the insertion, until the alignment pin snaps into the alignment hole. As further used herein, the term "being deformed" may refer to a property of an arbitrary element of having an altered shape that differs from an original shape of the element and wherein the altered shape is based on an external force applied to the element such as a mechanical force. Exemplarily, the original shape of the element may correspond to a plane shape and the altered shape may comprise a bent of the element caused by the mechanical force. Further, the term "snapping into something" may generally refer to a mechanism, wherein an element is placed into another object, such as into a receptacle or into a hole of the other object.

The term "open position" may refer to a position wherein the first part and the second part are spaced apart such that the test element may freely be removed from the test element receptacle. Specifically, in the open position, the alignment pin may be pulled out of the alignment hole completely and is therefore without any contact with the alignment hole even if the test element is moved in a plane parallel to the support surface, e.g., when the test element is removed from the test element receptacle. The term "being freely removed" may generally refer to a property of an arbitrary element of being taken from the other object without or at least almost without any resistance, specifically such that a user may be enabled to insert or to remove the element by applying only minor forces.

As further used therein, the term "closed position" may refer to a state, wherein the alignment pin protrudes through the alignment hole of the test element. In the closed position, the test element may be supported by the first part and the second part may rest on the test element. The test element analysis system may be configured to perform a measurement when the test element is inserted into the receptacle and the second part is into the closed position. Thereby, the term "performing a measurement" may refer to a property of an arbitrary device of detecting at least one signal. Exemplarily, the signal may be an optical signal and/or an electrochemical signal. Specifically, the signal may be utilized to determining the presence and/or the quantity and/or the concentration of the at least one analyte as described above.

Further, the test element analysis system may comprise at least one actuator for driving a relative movement of the first part and the second part. As further used herein, the term "actuator" refers to an arbitrary element that is configured to move, position or control an element, a mechanism or a system. Specifically, the actuator may be configured to move the second part from a first position to a second position and vice versa. The actuator may be operated by a source of energy, typically electric current or mechanical pressure and may convert energy into motion. The actuator may be selected from the group consisting of: a mechanical actuator, an electromagnetic actuator, a pneumatic actuator. However, other kinds of actuators may be applied. The actuator may be configured for performing a predetermined sequence of movements, sequentially bringing the first part and the second part into the intermediate position, into the closed position and into the open position. Therefore, the test element analysis system may comprise at least one controller for controlling the predetermined sequence of movements. Further, the actuator may be configured for stopping the movement in the intermediate position, in the closed position and in the open position, respectively. Specifically, the second part may be biased by at least one spring element against the first part, wherein the actuator is configured to act against the bias.

In accordance with another embodiment of the present disclosure, a method for positioning a test element in a measuring device for performing an analytical examination of a sample, in particular of a body fluid, is disclosed. The method may comprise using the test element analysis system as described above or as will further be described below. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method for positioning a test element in a measuring device for performing an analytical examination of a sample comprises the following steps:

a) providing a measurement device having a test element receptacle for receiving at least one test element at least partially, wherein the test element receptacle comprises at least one first part and at least one second part, wherein the first part comprises at least one support surface for placement of the test element, wherein the second part comprises at least one alignment pin for engagement with at least one alignment hole of the test element, wherein the second part is movable relative to the first part in a direction essentially perpendicular to the support surface, b) positioning the second part in an intermediate position, wherein in the intermediate position the first part and the second part are spaced apart such that the test element may be inserted into the test element receptacle, c) inserting at least one test element having at least one alignment hole into the test element receptacle, wherein the test element is temporarily and resiliently deformed by the alignment pin during the insertion, until the alignment pin snaps into the alignment hole, d) positioning the second part in a closed position, wherein in the closed position the alignment pin protrudes through the alignment hole, e) positioning the second part in an open position, wherein in the open position the first part and the second part are spaced apart, and f) removing the test element from the test element receptacle.

The term "temporarily" may generally refer to an arbitrary property of a process of lasting for a time only and of not being of permanent nature.

The positioning of the second part in the closed position may exemplarily be triggered by a light barrier. The light barrier may specifically be configured to recognize that the test element is inserted into the test element receptacle. Further, optionally, a removing of the test element from the test element receptacle of the test element analysis system may be supported by tilting the test element analysis system by the user or the patient or by applying a small physical force onto the test element by the user or the patient, which may be detected by respective sensors. However, other embodiments may be feasible.

In accordance with yet another embodiment of the present disclosure, a method for an analytical examination of a sample, in particular of a body fluid, is disclosed. The method comprises the method steps of the method for positioning a test element in a measuring device for performing an analytical examination of a sample as described above or as will further be described below. Further, the method comprises at least one measurement step for detecting at least one analyte in the sample. Specifically, the measurement step may be performed in between method steps d) and e). However, other embodiments may be feasible.

The proposed test element analysis system for the analytical examination of a sample as well as the proposed method for positioning a test element in a measuring device for performing an analytical examination of a sample and the proposed method for an analytical examination of a sample provide many advantages over known devices and methods.

Generally, in a common test element analysis system, such as a common optical measurement system, an optical area of a test element, specifically of a test strip, and an optical detection system of a measurement device such as a meter has to be aligned quite precisely. Further, in common test element analysis systems based on an electrochemical measurement system, the test element may normally be aligned by an electrical connector of the measurement device. However, thereby, a positioning of the test element in the measurement device may usually not be as precise as via an alignment pin.

In case both detection methods are used, the test element usually has to be aligned very well with regard to the optical measurement system and electrically coupled via the electrical connector. Usually, these two requirements may not easily be fulfilled together with common designs. Commonly, the electrical connector may not be precise enough and with an additional alignment pin, the test element may usually be fixed at two different positions and may therefore mechanically be overdetermined.

Exemplarily, a ZIF-connector (Zero Injection Force) may be applied. The ZIF-connector may specifically be advantageous as the alignment pin may be capable of mechanical positioning of the test element in the measurement device. Therefore, the test element can usually be aligned very well to the optical measurement system. However, also by applying the ZIF-connector, there may be several features that have to be ensured. Specifically between a time when the user inserts the test element and a connection to the electrical connector is existent, the position of the test element may be undefined, specifically because there may be a time delay between these two situations. Especially when the user is moving with a hand-held meter, there may be a high risk for this. This may be dangerous because the electrical connector or the test strip may get destroyed when the electrical connector closes. Further, the test element may have to be secured against any radial forces, e.g., when the user pulls at the test element. If this is the case, the electrical connector may get destroyed.

The test element analysis system according to the present disclosure may provide many advantages. Specifically, the test element may be secured via the alignment pin. The alignment pin may be movable in an axial direction. Specifically, there may be three different positions. In the intermediate position, the test element may be inserted into the test element receptacle, specifically by sliding over the tip of the alignment pin. Specifically, the tip may be conus shaped. If the alignment hole of the test element is located under the alignment pin, the alignment pin may snap into the defined position. The test element may be secured against falling out of the test element analysis system on its own. However, the user may be able to remove the test element with a little force.

In the closed position, the alignment pin may move down. Now, a gap between the alignment pin and the alignment hole of the test element may be minimized because a cylindrical part of the alignment pin may be located in the alignment hole. Therefore, the test element may be fixed and positioned very well within the test element analysis system. Even if the user pulls on the test element, a position of the test element within the test element analysis system may be stable.

Therefore, the test element may be secured. Further, an alignment of the test element to an optical detection system may be secured as well.

The alignment pin may move up until the tip of the alignment pin is completely out of the alignment hole of the test element when a measurement is finished. In the open position, the test element may be freely movable. Specifically, there may be no mechanical fixation of the test element by the alignment pin any more. In this position, the test element may be easily removable from the test element analysis system, specifically from the test element receptacle. Therefore, it may be secured that the ZIF-connector cannot be destroyed by the test element.

Summarizing the findings of the present disclosure, the following embodiments are typical:

Embodiment 1

A test element analysis system for the analytical examination of a sample, comprising a measurement device, the measurement device comprising a test element receptacle for receiving at least one test element, specifically a test strip, at least partially, wherein the test element receptacle comprises at least one first part and at least one second part, wherein the first part comprises at least one support surface for placement of the test element, wherein the second part comprises at least one alignment pin for engagement with at least one alignment hole of the test element, wherein the second part is movable relative to the first part in a direction essentially perpendicular to the support surface, wherein the test element receptacle is configured to position the second part in at least three distinct positions relative to the first part, the at least three distinct positions comprising an intermediate position for inserting the test element into the test element receptacle, a closed position for performing a measurement and an open position for removing the test element from the test element receptacle,
wherein in the closed position the alignment pin protrudes through the alignment hole,
wherein in the open position the first part and the second part are spaced apart such that the test element may freely be removed from the test element receptacle, and
wherein in the intermediate position the first part and the second part are spaced apart such that the test element may be inserted into the test element receptacle, whereas the alignment pin is positioned such that the test element is resiliently deformed by the alignment pin during the insertion, until the alignment pin snaps into the alignment hole.

Embodiment 2

The test element analysis system according to the preceding embodiment, wherein the test element analysis system further comprises at least one test element having the at least one alignment hole.

Embodiment 3

The test element analysis system according to the preceding embodiment, wherein the test element is a test strip.

Embodiment 4

The test element analysis system according to any one of the two preceding embodiments, wherein the test element has at least one test field comprising at least one test chemical for performing at least one detection reaction in the presence of an analyte contained in the sample, specifically glucose.

Embodiment 5

The test element analysis system according to the preceding embodiment, wherein the test chemical is configured for performing at least one of an optical detection reaction and an electrochemical detection reaction.

Embodiment 6

The test element analysis system according to any one of the preceding embodiments, wherein in the closed position the test element is supported by the first part and the second part rests on the test element.

Embodiment 7

The test element analysis system according to any one of the preceding embodiments, wherein, in the open position, the alignment pin is pulled out of the alignment hole completely.

Embodiment 8

The test element analysis system according to any one of the preceding embodiments, wherein the test element receptacle further comprises a lateral guiding for the test element, wherein the lateral guiding prevents at least to a large extent a rotation of the test element within the test element receptacle when the alignment hole is engaged by the alignment pin.

Embodiment 9

The test element analysis system according to the preceding embodiment, wherein the lateral guiding comprises a sidewall of the test element receptacle.

Embodiment 10

The test element analysis system according to any one of the preceding embodiments, wherein the second part comprises a block that is linearly movable in the direction essentially perpendicular to the support surface, wherein the alignment pin is at least partially integrated into the block.

Embodiment 11

The test element analysis system according to any one of the preceding embodiments, wherein the measurement device comprises at least one detector for detecting at least one detection reaction between the sample or at least one component thereof and at least one constituent of the test element, specifically at least one test chemical of the test element.

Embodiment 12

The test element analysis system according to the preceding embodiment, wherein the at least one detector is fully or partially comprised in the second part.

Embodiment 13

The test element analysis system according to any one of the two preceding embodiments, wherein the alignment pin is configured to position the test element relative to the at least one detector.

Embodiment 14

The test element analysis system according to any one of the preceding embodiments, wherein the support surface is an essentially flat surface.

Embodiment 15

The test element analysis system according to any one of the preceding embodiments, wherein the second part comprises at least one abutment surface interacting with the support surface in the closed position, wherein, in the closed position, the abutment surface rests on the test element.

Embodiment 16

The test element analysis system according to the preceding embodiment, wherein the abutment surface is essentially parallel to the support surface.

Embodiment 17

The test element analysis system according to any one of the two preceding embodiments, wherein the alignment pin protrudes from the abutment surface.

Embodiment 18

The test element analysis system according to any one of the three preceding embodiments, wherein the alignment pin is located essentially perpendicular to the abutment surface.

Embodiment 19

The test element analysis system according to any one of the preceding embodiments, wherein a tip of the alignment pin, in the intermediate position, penetrates a plane through the support surface, wherein, in the open position, the alignment pin does not penetrate the plane through the support surface.

Embodiment 20

The test element analysis system according to any one of the preceding embodiments, wherein the second part is movable in a linear fashion relative to the first part.

Embodiment 21

The test element analysis system according to any one of the preceding embodiments, wherein the test element receptacle contains at least one guiding element for guiding a relative movement of the second part and the first part.

Embodiment 22

The test element analysis system according to the preceding embodiment, wherein the guiding element comprises at least one guide rail, more typically at least one linear guide rail.

Embodiment 23

The test element analysis system according to any one of the preceding embodiments, wherein the test element analysis system further comprises at least one actuator for driving a relative movement of the first part and the second part.

Embodiment 24

The test element analysis system according to the preceding embodiment, wherein the actuator is configured for performing a predetermined sequence of movements, sequentially bringing the first part and the second part into the intermediate position, into the closed position and into the open position.

Embodiment 25

The test element analysis system according to the preceding embodiment, wherein the actuator is configured for stopping the movement in the intermediate position, in the closed position and in the open position, respectively.

Embodiment 26

The test element analysis system according to any one of the two preceding embodiments, wherein the test element analysis system comprises at least one controller for controlling the predetermined sequence of movements.

Embodiment 27

The test element analysis system according to any one of the four preceding embodiments, wherein the second part is biased by at least one spring element against the first part, wherein the actuator is configured to act against the bias.

Embodiment 28

The test element analysis system according to any one of the preceding embodiments, wherein the alignment pin is a cylindrical alignment pin, typically a cylindrical alignment pin having a circular cross-section.

Embodiment 29

The test element analysis system according to any one of the preceding embodiments, wherein the alignment pin has at least one tapered tip.

Embodiment 30

The test element analysis system according to the preceding embodiment, wherein the tapered tip has a shape selected from the group consisting of a conical shape, a round shape, a tapered tip with a one-sided flat slope.

Embodiment 31

The test element analysis system according to any one of the preceding embodiments, wherein the alignment pin has a cylindrical portion and a tapered tip, wherein, in the closed position, the cylindrical portion is inside the alignment hole, wherein, in the intermediate position, after the alignment pin has snapped into the alignment hole, the tapered tip is inside the alignment hole.

Embodiment 32

The test element analysis system according to any one of the preceding embodiments, wherein the test element receptacle further comprises at least one abutment element, wherein the abutment element, in the intermediate position, is configured for limiting an insertion of the test element into the test element receptacle.

Embodiment 33

The test element analysis system according to the preceding embodiment, wherein the abutment element is movable in a direction of insertion of the test element, wherein the abutment element is configured for ejecting the test element after use, when the test element receptacle is in the open position.

Embodiment 34

The test element analysis system according to any one of the preceding embodiments, wherein the first part forms a fixed subassembly and wherein the second part forms a movable subassembly of the test element receptacle.

Embodiment 35

The test element analysis system according to any one of the preceding embodiments, wherein the measurement device further comprises at least one evaluation device for evaluating at least one measurement performed with the measurement device, specifically at least one processor.

Embodiment 36

A method for positioning a test element in a measuring device for performing an analytical examination of a sample, in particular a body fluid, the method comprising
 a) providing a measurement device having a test element receptacle for receiving at least one test element at least partially, wherein the test element receptacle comprises at least one first part and at least one second part, wherein the first part comprises at least one support surface for placement of the test element, wherein the second part comprises at least one alignment pin for engagement with at least one alignment hole of the test element, wherein the second part is movable relative to the first part in a direction essentially perpendicular to the support surface,
 b) positioning the second part in an intermediate position, wherein in the intermediate position the first part and the second part are spaced apart such that the test element may be inserted into the test element receptacle,
 c) inserting at least one test element having at least one alignment hole into the test element receptacle, wherein the test element is temporarily and resiliently deformed by the alignment pin during the insertion, until the alignment pin snaps into the alignment hole, d) positioning the second part in a closed position, wherein in the closed position the alignment pin protrudes through the alignment hole, e) positioning the second part in an open position, wherein in the open position the first part and the second part are spaced apart, and f) removing the test element from the test element receptacle.

Embodiment 37

The method according to the preceding embodiments, wherein the method comprises using the test element analysis system according to any one of the preceding embodiments referring to a test element analysis system.

Embodiment 38

A method for an analytical examination of a sample, in particular of a body fluid, wherein the method comprises the method steps according to any one of the preceding embodiments referring to a method for positioning a test element in a measuring device for performing an analytical examination of a sample, wherein the method further comprises at least one measurement step for detecting at least one analyte in the sample.

Embodiment 39

The method according to the preceding embodiment, wherein the measurement step is performed in between method steps d) and e) of the method for positioning a test element in a measuring device for performing an analytical examination of a sample.

In order that the embodiments of the disclosure may be more readily understood, reference is made to the following examples, which are intended to illustrate but not limit the scope thereof.

FIG. 1A shows a test element analysis system 110 for the analytical examination of a sample in a cross-sectional view. Further, FIG. 1B shows a detailed view of a part 112 of the test element analysis system 110 of FIG. 1A in a cross-sectional view. The test element analysis system 110 comprises a measurement device 114. The measurement device 114 comprises a test element receptacle 116 for receiving at least one test element 118 at least partially. The test element 118 may specifically be a test strip 120. The test element receptacle 116 comprises at least one first part 122 and at least one second part 124. The first part 122 may form a fixed subassembly 125 and the second part may form a movable subassembly 127 of the test element receptacle 116. The first part 122 comprises at least one support surface 126 for placement of the test element 118. The second part 124 comprises at least one alignment pin 128 for engagement with at least one alignment hole 130 of the test element 118. The second part 124 is movable relative to the first part 122 in a direction 132 essentially perpendicular to the support surface 126. Further, the test element receptacle 116 is configured to position the second part 124 in at least three distinct positions relative to the first part 122. In FIGS. 1A and 1B an intermediate position 134 of the second part 124 is shown. In the intermediate position 134, the first part 122 and the second part 124 are spaced apart such that the test element 118 may be inserted into the test element receptacle 116. Thereby, the alignment pin 128 is positioned such that the test element 118 is temporarily deformed by the alignment pin 128 during the insertion, until the alignment pin 128 snaps into the alignment hole 130 (as shown in FIGS. 1A and 1B).

The second part 124 may comprise a block 136, which is linearly movable in the direction 132 essentially perpendicular to the support surface. Specifically, the alignment pin 128 may be at least partially embedded and/or integrated into the block 136. In another embodiment, the alignment pin 128 is not a separate part, but the block 136 itself has a geometry that forms the alignment pin 128. The measurement device 114 may comprise at least one detector 138 for detecting at least one detection reaction between the sample or at least one component thereof and at least one constituent 140 of the test element 118, specifically at least one test chemical 142 of the test element 118. The detector 138 may be fully or partially comprised in the second part 124, specifically in the block 136. The detector 138 may exemplarily be an optical detector 144.

The alignment pin 128 may specifically be a cylindrical alignment pin 146. The cylindrical alignment pin 146 may have a circular cross-section. Further, the alignment pin 130 may have a tip 148. The tip 148 may specifically be a tapered tip 150. In the intermediate position 134, the tip 148 of the alignment pin 128 may penetrate a plane 152 through the support surface 126. Further, in the intermediate position 134, as the alignment pin 128 has snapped into the alignment hole 130 of the test element 118, the tapered tip 150 may be inside the alignment hole 130. Thus, in the intermediate position 134, the first part 122 and the second part 124 may be spaced apart such that the test element 118 may be inserted into the test element receptacle 116.

The support surface 126 may specifically be an essentially flat surface 154. The second part 124 may comprise at least one abutment surface 156. The abutment surface 156 may be essentially parallel to the support surface 126. Further, the alignment pin 128 may protrude from the abutment surface 156. Specifically, the alignment pin 128 may be located essentially perpendicular to the abutment surface 156.

The test element receptacle 116 may further comprise a lateral guiding 158 for the test element 118. The lateral guiding 158 may be configured to prevent, at least to a large extent, a rotation of the test element 118 within the test element receptacle 116 when the alignment hole 130 of the test element 118 is engaged by the alignment pin 128. Specifically, the lateral guiding 158 may comprise a side wall 160 of the test element receptacle 116. Specifically, the lateral guiding 158 may be positioned relative to longitudinal sides (not shown) of the test element 118 and may be configured to prevent a rotation of the test element 116 around the alignment pin 128 at least partially.

Further, the test element analysis system 110 may comprise at least one actuator 162 for driving a relative movement of the first part 122 and the second part 124. Specifically, the actuator 162 may be configured for performing a predetermined sequence of movements, sequentially bringing the first part 122 and the second part 124 into the intermediate position 134 and into further positions as will further be described in FIGS. 2A to 3B.

FIG. 2A shows the test element analysis system 110 as illustrated in FIGS. 1A and 1B in a cross-sectional view. Thus, reference may be made to the description of FIGS. 1A to 1B above. However, in FIG. 2A, the second part 124 is in a closed position 164. FIG. 2B shows a detailed view of the part 112 of the test element analysis system of FIG. 2A.

In the closed position 164 the alignment pin protrudes through the alignment hole 130. Specifically, the test element 118 may be supported by the first part 122 and the second part 124 may rest on the test element 118. Specifically, the abutment surface 156 may be configured to interact with the support surface 126. Thereby the abutment surface 156 may be configured to rest on the test element 118. The test element 118 may be fixed and positioned within the test element receptacle 116. Even if a user pulls on the test element 118, the position of the test element 118 within the test element receptacle 116 may be stable. In the closed position 164, a measurement, specifically a measurement for detecting at least one analyte in a sample may be conducted, specifically via the measurement device 114.

FIG. 3A shows the test element analysis system 110 as illustrated in FIGS. 1A to 2B in a cross-sectional view. Thus, reference may be made to the description of FIGS. 1A to 2B above. However, in FIG. 3A, the second part 124 is in the open position 166. FIG. 3B shows a detailed view of the part 112 of the test element analysis system of FIG. 3A.

In the open position 166, the first part 122 and the second part 124 are spaced apart such that the test element 118 may freely be removed from the test element receptacle 116. Specifically, in the open position 166, the alignment pin 128 may be pulled out of the alignment hole 130 completely. In the open position 166, the test element 118 may be removed from test element receptacle 116. There may be no mechanical fixation of the test element any more.

Figure 4:
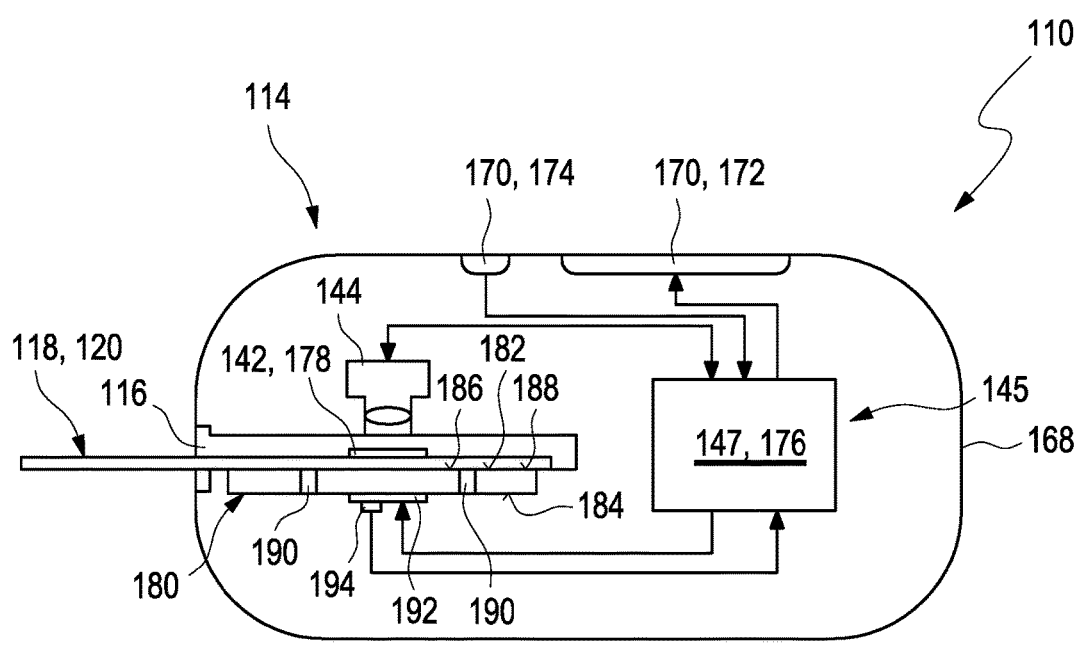
FIG. 4 shows details of an exemplary embodiment of a test element analysis system in a cross-sectional view.

In FIG. 4, details of a cross-sectional view of a simplified embodiment of a test element analysis system 110 for the analytical examination of a sample is shown. The test element analysis system 110 comprises a housing 168 with user interfaces 170, such as a display 172 and one or more control elements 174. The test element analysis system 110 may comprise at least one controller 176 which, as an example, may fully or partially be configured as an evaluation device 145 for evaluating the analysis, specifically at least one processor 147. The controller 176 may be connected to the user interfaces 170. The evaluation device 145 may be part of a measurement device 114.

The test element analysis system 110 may further comprise the at least one test element receptacle 116 for receiving the test elements 118. The test element analysis system 110 further may comprise the optical detector 144 for detecting at least one analytical reaction of the sample with the at least one test chemical 142 comprised by the test element 118, such as the at least one test chemical 142 contained in at least one test field 178.

The test element 118 specifically may be designed as test strip 120. The optical detector 144 may have at least one light source (not depicted) and at least one optical sensor, for performing remission measurements on the test field 178.

The test element analysis system 110 may further comprise at least one heating element 180 for heating the test element 118. The heating element 180 may comprise a front face 182, facing the test element 118, on which the test element 118 may rest, and, on an opposing side, a back face 184.

On the front face 182, an active area 186 may be defined that faces the region of the test element 118 containing the test field 178. Outside the active area 186, a non-active area 188 may be defined. The active area 186 may be separated from the non-active area 188 by at least one thermal insulation element 190.

On the back face 184, the heating element 180 may comprise one or more heaters 192. Further, the heating element 180 may comprise one or more thermal sensor elements 194 for detecting a temperature of the heating element 180. The heater 192 and the thermal sensor element 194 may both directly or indirectly be connected to the controller 176.

LIST OF REFERENCE NUMBERS 110 test element analysis system
112 part
114 measurement device
116 test element receptacle
118 test element
120 test strip
122 first part
124 second part
125 fixed subassembly
126 support surface
127 movable subassembly
128 alignment pin
130 alignment hole
132 direction
134 intermediate position
136 block
138 detector
140 constituent
142 test chemical
144 optical detector
145 evaluation device
146 cylindrical alignment pin
147 processor
148 tip
150 tapered tip
152 plane
154 essentially flat surface
156 abutment surface
158 lateral guiding
160 side wall
162 actuator
164 closed position
166 open position
168 housing
170 user interface
172 display
174 control element
176 controller
178 test field
180 heating element
182 front face
184 back face
186 active area
188 non-active area
190 thermal insulation element
192 heater
194 thermal sensor element It is noted that terms like "preferably," "commonly" and typically are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

For purposes of describing and defining the subject matter of the present disclosure it is noted that the terms "substantially" and "about" may be utilized herein to represent the inherent degree of uncertainly that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus, it is intended that the specification cover the modifications and variations of the various embodiments described herein, provided such modifications and variations come within the scope of the appended claims and their equivalents.

What is claimed is:

1. A test element analysis system for the analytical examination of a sample, comprising a measurement device, the measurement device comprising a test element receptacle for receiving at least one test element at least partially, wherein the test element receptacle comprises at least one first part and at least one second part, wherein the first part comprises at least one support surface for placement of the test element, wherein the second part comprises at least one alignment pin for engagement with at least one alignment hole of the test element, wherein the second part is movable relative to the first part in a direction essentially perpendicular to the support surface, wherein the test element receptacle is configured to position the second part in at least three distinct positions relative to the first part, the at least three distinct positions comprising an intermediate position for inserting the test element into the test element receptacle, a closed position for performing a measurement and an open position for removing the test element from the test element receptacle, wherein in the closed position the alignment pin protrudes through the alignment hole, wherein in the open position the first part and the second part are spaced apart such that the test element may freely be removed from the test element receptacle, and wherein in the intermediate position the first part and the second part are spaced apart such that the test element may be inserted into the test element receptacle, whereas the alignment pin is positioned such that the test element is resiliently deformed by the alignment pin during the insertion, until the alignment pin snaps into the alignment hole.

2. The test element analysis system according to claim 1, wherein the test element analysis system further comprises at least one test element having the at least one alignment hole.

3. The test element analysis system according to claim 1, wherein in the closed position the test element is supported by the first part, and the second part rests on the test element.

4. The test element analysis system according to claim 1, wherein in the open position the alignment pin is pulled out of the alignment hole completely.

5. The test element analysis system according to claim 1, wherein the test element receptacle further comprises a lateral guiding for the test element, wherein the lateral guiding prevents at least to a large extent a rotation of the test element within the test element receptacle when the alignment hole is engaged by the alignment pin.

6. The test element analysis system according to claim 1, wherein the second part comprises a block that is linearly movable in the direction essentially perpendicular to the support surface, and the alignment pin is at least partially integrated into the block.

7. The test element analysis system according to claim 1, wherein the measurement device comprises at least one detector for detecting at least one detection reaction between the sample or at least one component thereof, and at least one constituent of the test element.

8. The test element analysis system according to claim 7, wherein the at least one detector is fully or partially comprised in the second part.

9. The test element analysis system according to claim 7, wherein the alignment pin is configured to position the test element relative to the at least one detector.

10. The test element analysis system according to claim 1, wherein the second part comprises at least one abutment surface interacting with the support surface in the closed position, and wherein, in the closed position, the abutment surface rests on the test element.

11. The test element analysis system according to claim 1, wherein a tip of the alignment pin, in the intermediate position, penetrates a plane through the support surface, and wherein, in the open position, the alignment pin does not penetrate the plane through the support surface.

12. The test element analysis system according to claim 1, wherein the test element receptacle contains at least one guiding element for guiding a relative movement of the second part and the first part.

13. The test element analysis system according to claim 1, wherein the test element analysis system further comprises at least one actuator for driving a relative movement of the first part and the second part.

14. A method for positioning a test element in a measuring device for performing an analytical examination of a sample, the method comprising:
   a) providing a measurement device having a test element receptacle for receiving at least one test element at least partially, wherein the test element receptacle comprises at least one first part and at least one second part, wherein the first part comprises at least one support surface for placement of the test element, wherein the second part comprises at least one alignment pin for engagement with at least one alignment hole of the test element, and wherein the second part is movable relative to the first part in a direction essentially perpendicular to the support surface,
   b) positioning the second part in an intermediate position, wherein in the intermediate position the first part and the second part are spaced apart such that the test element may freely be inserted into the test element receptacle,
   c) inserting at least one test element having at least one alignment hole into the test element receptacle, wherein the test element is temporarily and resiliently deformed by the alignment pin during the insertion, until the alignment pin snaps into the alignment hole,
   d) positioning the second part in a closed position, wherein in the closed position the alignment pin protrudes through the alignment hole,
   e) positioning the second part in an open position, wherein in the open position the first part and the second part are spaced apart, and
   f) removing the test element from the test element receptacle.

15. The method according to claim 14, wherein the sample is a sample of a body fluid.

16. A method for an analytical examination of a sample, wherein the method comprises the method steps according to claim 14, and wherein the method further comprises at least one measurement step for detecting at least one analyte in the sample.

* * * * *